United States Patent
Otsugu et al.

(10) Patent No.: US 9,708,246 B2
(45) Date of Patent: Jul. 18, 2017

(54) METHOD FOR RECOVERING FLUORINATED EMULSIFIER

(71) Applicant: Asahi Glass Company, Limited, Chiyoda-ku (JP)

(72) Inventors: Satoshi Otsugu, Chiyoda-ku (JP); Mizuna Toyoda, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 15/075,655

(22) Filed: Mar. 21, 2016

(65) Prior Publication Data

US 2016/0200669 A1   Jul. 14, 2016

Related U.S. Application Data

(63) Continuation of application No. PCT/JP2014/076728, filed on Oct. 6, 2014.

(30) Foreign Application Priority Data

Oct. 10, 2013   (JP) ................ 2013-212673

(51) Int. Cl.
*C07C 235/06* (2006.01)
*B01D 15/36* (2006.01)
*C07C 51/47* (2006.01)
*B01J 41/05* (2017.01)
*B01J 49/07* (2017.01)
*B01J 49/57* (2017.01)
*B01J 49/60* (2017.01)

(52) U.S. Cl.
CPC .......... *C07C 235/06* (2013.01); *B01D 15/363* (2013.01); *B01J 41/05* (2017.01); *B01J 49/07* (2017.01); *B01J 49/57* (2017.01); *B01J 49/60* (2017.01); *C07C 51/47* (2013.01)

(58) Field of Classification Search
CPC .... C07C 235/06; C07C 51/47; B01J 49/0078; B01J 49/0013; B01J 49/0073; B01J 41/03; B01J 41/05; B01J 49/07; B01J 49/57; B01J 49/60; B01D 15/363
See application file for complete search history.

(56) References Cited

U.S. PATENT DOCUMENTS

| | | | |
|---|---|---|---|
| 4,282,162 A | 8/1981 | Kuhls | |
| 9,045,411 B2* | 6/2015 | Aida | ............ B01J 41/043 |
| 2004/0010156 A1 | 1/2004 | Kondo et al. | |
| 2007/0282055 A1 | 12/2007 | Teter et al. | |
| 2008/0182913 A1 | 7/2008 | Higuchi et al. | |
| 2010/0047585 A1* | 2/2010 | Hintzer | ............ C08F 6/16 |
| | | | 428/421 |
| 2012/0271065 A1 | 10/2012 | Haga et al. | |

FOREIGN PATENT DOCUMENTS

| | | |
|---|---|---|
| DE | 2 044 986 | 3/1971 |
| JP | 47-51233 | 12/1972 |
| JP | 2002-59160 | 2/2002 |
| JP | 2009-538965 | 11/2009 |
| WO | WO 99/62830 | 12/1999 |
| WO | WO 2007/043278 A1 | 4/2007 |
| WO | WO 2011/096448 A1 | 8/2011 |

OTHER PUBLICATIONS

English Translation of International Search Report issued Dec. 9, 2014 in PCT/JP2014/076728, filed Oct. 6, 2014.
Diaion Manual of Ion Exchange Resins and Synthetic Absorbent I Kisohen, 5th ed., Mitsubishi Kasei Corp. Jun. 1, 1992, 9 pages.

* cited by examiner

*Primary Examiner* — Paul A Zucker
*Assistant Examiner* — Mark Luderer
(74) *Attorney, Agent, or Firm* — Oblon, McClelland, Maier & Neustadt, L.L.P.

(57) ABSTRACT

To provide a method for recovering, from a liquid to be treated containing a fluorinated polymer and a fluorinated emulsifier, the fluorinated emulsifier easily and efficiently. A liquid to be treated containing a fluorinated polymer and a fluorinated emulsifier, and a strongly basic anion exchange resin having an ion exchange capacity of at most 1.0 eq/L and a water content of at least 60 mass %, are brought into contact with each other, so that the fluorinated emulsifier is adsorbed on the strongly basic anion exchange resin, whereby the fluorinated emulsifier is recovered from the liquid to be treated.

20 Claims, No Drawings

METHOD FOR RECOVERING FLUORINATED EMULSIFIER

TECHNICAL FIELD

The present invention relates to a method for recovering a fluorinated emulsifier.

BACKGROUND ART

A method for recovering, from a waste water containing a fluorinated emulsifier, the fluorinated emulsifier by an anion exchange resin (hereinafter referred to as IER) has been known.

For example, a method of adsorbing a fluorinated emulsifier such as ammonium perfluorooctanoate (hereinafter referred to as APFO) on an IER and recovering the fluorinated emulsifier contained in a waste water (hereinafter sometimes referred to as coagulation waste water) resulting from an aqueous dispersion containing a fluorinated polymer and the fluorinated emulsifier, obtained by coagulating the fluorinated polymer in the aqueous dispersion to form coagulum and recovering the coagulum has been known (Patent Documents 1 to 3).

However, the coagulation waste water contains SS (suspended solid) components such as non-coagulated fine particles of the fluorinated polymer and coagulated particles of the fluorinated polymer having small particle sizes which had passed the filter. Accordingly, when the fluorinated emulsifier contained in the coagulation waste water is adsorbed on an IER, the surface of the IER is covered with the SS components, whereby problems arise such that a column packed with the IER is clogged, and the adsorption performance of the IER decreases. If such problems arise, the fluorinated emulsifier may not efficiently be recovered from the coagulation waste water.

To overcome such problems, the following methods have been proposed (Patent Document 4).

(1) A method of adding a nonionic surfactant or a cationic surfactant to the coagulation waste water to stabilize fine particles of polytetrafluoroethylene (hereinafter referred to as PTFE) contained in the coagulation waste water to suppress clogging of the column packed with the IER.

(2) A method for pretreating a coagulation waste water by adding lime water to a coagulation waste water containing a tetrafluoroethylene/perfluoro(alkyl vinyl ether) copolymer (hereinafter referred to as PFA) to adjust the pH to be from 6 to 7.5, adding a metal salt such as aluminum chloride to coagulate non-coagulated PFA, mechanically separating the coagulum, and adjusting the pH of the coagulation waste water to be at most 7 with sulfuric acid.

However, it is not possible by the method (1) to sufficiently suppress clogging of the packed column, the decrease in the adsorption performance of the IER, etc.

The method (2) is not easily conducted. Further, since the SS components cannot sufficiently be removed, if a large amount of the coagulation waste water is treated with the IER, the column packed with the IER will be clogged, and the adsorption performance of the IER will decrease.

PRIOR ART DOCUMENTS

Patent Documents

Patent Document 1: JP-B-47-51233
Patent Document 2: U.S. Pat. No. 4,282,162
Patent Document 3: German Patent No. 2,044,986
Patent Document 4: WO99/62830

DISCLOSURE OF INVENTION

Technical Problem

The object of the present invention is to provide a method for recovering, from a liquid to be treated containing a fluorinated polymer and a fluorinated emulsifier, the fluorinated emulsifier easily and efficiently.

Solution to Problem

The method for recovering a fluorinated emulsifier of the present invention is a method for recovering, from a liquid to be treated containing a fluorinated polymer and a fluorinated emulsifier, the fluorinated emulsifier, which comprises bringing the liquid to be treated and a strongly basic IER having an ion exchange capacity of at most 1.0 eq/L and a water content of at least 60 mass % into contact with each other, so that the fluorinated emulsifier is adsorbed on the strongly basic IER.

In the method for recovering a fluorinated emulsifier of the present invention, it is preferred that the fluorinated emulsifier is adsorbed on the strongly basic anion exchange resin, and then the fluorinated emulsifier adsorbed on the strongly basic anion exchange resin is eluted from the strongly basic anion exchange resin.

The liquid to be treated is preferably a waste water resulting from an aqueous dispersion containing the fluorinated polymer and the fluorinated emulsifier, obtained by coagulating the fluorinated polymer in the aqueous dispersion to form coagulum and recovering the coagulum.

The concentration of the fluorinated emulsifier in the liquid to be treated is preferably from 10 to 5,000 ppm.

The ratio (the strongly basic IER/the liquid to be treated) of the strongly basic IER to the liquid to be treated is from 1/100 to 1/5,000 (mass ratio).

The fluorinated emulsifier is preferably a fluorinated carboxylic acid, a fluorinated sulfonic acid or a salt thereof.

The fluorinated carboxylic acid is preferably a perfluoroalkylcarboxylic acid or a perfluoroalkylcarboxylic acid having an etheric oxygen atom between carbon atoms.

The counter ion of the strongly basic IER is preferably $OH^-$ or $Cl^-$.

The strongly basic anion exchange resin preferably has quaternary ammonium groups on its side chains as ion exchange groups.

The average particle size of the strongly basic anion exchange resin is preferably from 0.1 to 5 mm.

Advantageous Effects of Invention

According to the method for recovering a fluorinated emulsifier of the present invention, from a liquid to be treated containing a fluorinated polymer and a fluorinated emulsifier, the fluorinated emulsifier can be recovered easily and efficiently.

DESCRIPTION OF EMBODIMENTS

The following definitions of terms are applicable throughout description and claims.

The "strongly basic anion exchange resin (IER)" means an ion exchange resin (IER) having quaternary ammonium groups.

The "counter ion of the strongly basic anion exchange resin (IER)" means an anion which is dissociated from the quaternary ammonium group and is capable of being exchanged with an outside anion.

The "fluorinated polymer" means a polymer having fluorine atoms in its molecule.

The "fluorinated emulsifier" means a compound having fluorine atoms in its molecule among compounds which can emulsify water and an oil to form a stable emulsion.

The "aqueous dispersion" means a dispersion having a dispersoid (fluorinated polymer) dispersed in an aqueous dispersion medium.

The "aqueous dispersion medium" means a medium consisting of water and as the case requires a water-soluble organic solvent.

<Method for Recovering Fluorinated Emulsifier>

The method for recovering a fluorinated emulsifier of the present invention is a method comprising the following steps (a) and (b).

Step (a): A step of bringing a liquid to be treated containing a fluorinated polymer and a fluorinated emulsifier, and a strongly basic IER having an ion exchange capacity of at most 1.0 eq/L and a water content of at least 60 mass %, into contact with each other, so that the fluorinated emulsifier is adsorbed on the strongly basic IER.

Step (b): A step of eluting the fluorinated emulsifier adsorbed on the strongly basic IER from the strongly basic IER as the case requires after the step (a).

(Step (a))

As the method of bringing the liquid to be treated and the strongly basic IER into contact with each other, for example, the following methods may be mentioned.

(1) A method of pouring the strongly basic IER into the liquid to be treated, followed by stirring (batch method).

(2) A method of passing the liquid to be treated through a packed column packed with the strongly basic IER (continuous method).

The time of contact of the liquid to be treated and the strongly basic IER is preferably from 10 to 240 minutes, more preferably from 30 to 180 minutes, most preferably from 30 to 120 minutes. When the contact time is at least 10 minutes, the fluorinated emulsifier can be sufficiently recovered. When the contact time is at most 240 minutes, the fluorinated emulsifier can be recovered efficiently in a short time.

Liquid to be Treated:

As the liquid to be treated, an aqueous dispersion containing a fluorinated polymer and a fluorinated emulsifier; a coagulation waste water obtained by coagulating the fluorinated polymer in the aqueous dispersion to form coagulum and recovering the coagulum, etc. may be mentioned, and preferred is a coagulation waste water, whereby the fluorinated emulsifier can be efficiently recovered.

As the aqueous dispersion, an aqueous dispersion obtained by subjecting a fluorinated monomer and as the case requires a monomer other than the fluorinated monomer to emulsion polymerization or aqueous dispersion polymerization in an aqueous dispersion medium in the presence of the fluorinated emulsifier may be mentioned.

As a method of coagulating the fluorinated polymer in the aqueous dispersion, a known method (such as a method of using a coagulant) may be mentioned.

As the method of recovering the coagulum, a known method (such as filtration) may be mentioned.

The coagulation waste water may be subjected to a pretreatment to reduce SS components (for example, the pretreatment as disclosed in Patent Document 4), however, it is preferred not to conduct such a pretreatment, with a view to easily recovering the fluorinated emulsifier.

Fluorinated Polymer:

As the fluorinated polymer, for example, a polymer having structural units derived from a fluorinated monomer and as the case requires structural units derived from a monomer other than the fluorinated monomer may be mentioned.

As the fluorinated monomer, for example, the following may be mentioned.

Fluoroethylene: Tetrafluoroethylene (hereinafter referred to as TFE), $CF_2=CFCl$, $CFH=CF_2$, $CFH=CH_2$, $CF_2=CH_2$ (hereinafter referred to as VdF) and the like.

Fluoropropylene: Hexafluoropropylene (hereinafter referred to as HFP), $CF_2=CHCF_3$, and the like.

$C_{3-10}$ perfluorovinylether: $CF_2=CFOCF_3$, $CF_2=CFOCF_2CF_3$, $CF_2=CFO(CF_2)_2CF_3$ (hereinafter referred to as PPVE), $CF_2=CFO(CF_2)_4CF_3$ and the like.

$C_{4-10}$ (perfluoroalkyl)ethylene: $CH_2=CH(CF_2)_4F$, $CH_2=CH(CF_2)_6F$ and the like.

$C_{4-10}$ polyfluoroalkylethylene (excluding (perfluoroalkyl) ethylene): $CH_2=CF(CF_2)_3H$ and the like.

Such fluorinated monomers may be used alone or in combination of two or more.

As other monomer, for example, the following may be mentioned.

Vinyl ester: Vinyl acetate and the like.

Vinyl ether: Ethyl vinyl ether, cyclohexyl vinyl ether, hydroxybutyl vinyl ether and the like.

Monomer having cyclic structure: Norbornene, norbornadiene and the like. Allyl ether: Methyl allyl ether and the like.

Olefin: Ethylene (hereinafter referred to as E), propylene (hereinafter referred to as P), isobutylene and the like.

Such other monomers may be used alone or in combination of two or more.

As the fluorinated polymer, PTFE, a TFE/P copolymer, a TFE/P/VdF copolymer, a TFE/HFP copolymer, a TFE/PPVE copolymer, an E/TFE copolymer, a VdF homopolymer, a TFE/HFP/VdF copolymer or a VdF/HFP copolymer may be mentioned.

As the fluorinated polymer, preferred is PTFE, a TFE/P copolymer, a TFE/P/VdF copolymer, a TFE/PPVE copolymer, an E/TFE copolymer or a TFE/HFP copolymer, and particularly preferred is PTFE, in view of a high concentration of the fluorinated emulsifier in the coagulation waste water and a high adsorption efficiency of the strongly basic IER.

Fluorinated Emulsifier:

As the fluorinated emulsifier, preferred is an anionic fluorinated emulsifier, more preferred are a fluorinated carboxylic acid, a fluorinated sulfonic acid, and a salt thereof, in view of a high recovery efficiency when the strongly basic anion exchange resin is used.

As the fluorinated carboxylic acid, a perfluoroalkylcarboxylic acid, a polyfluorocarboxylic acid having an etheric oxygen atom between carbon atoms, an ω-hydroperfluoroalkylcarboxylic acid or an ω-chloroperfluoroalkylcarboxylic acid may be mentioned. Preferred is a perfluoroalkylcarboxylic acid or a perfluoroalkylcarboxylic acid having an etheric oxygen atom between carbon atoms, whereby a hydrophobic perfluoroalkyl group is easily adsorbed on the hydrophobic surface of the strongly basic IER.

As the polyfluorocarboxylic acid having an etheric oxygen atom between carbon atoms, more preferable is a perfluorocarboxylic acid having all the hydrogen atoms bonded to carbon atoms constituting the molecular skeleton of the carboxylic acid substituted with fluorine atoms, or a polyfluorocarboxylic acid having one hydrogen atom bonded to a carbon atom remaining.

As the fluorinated sulfonic acid, a perfluoroalkylsulfonic acid may be mentioned. The fluorinated emulsifier is preferably a $C_{5-13}$ fluorinated emulsifier, more preferably a $C_{6-12}$ fluorinated emulsifier in view of an excellent effect as the emulsifier.

The fluorinated emulsifier may have a linear structure, a branched structure or a mixture thereof. It may have an etheric oxygen atom between carbon atoms.

The salt of the acid is preferably an alkali metal salt (such as lithium salt, sodium salt or potassium salt) or an ammonium salt, more preferably an ammonium salt or a sodium salt, particularly preferably an ammonium salt, in view of easy dissociation in the liquid to be treated.

As the perfluoroalkylcarboxylic acid, for example, specifically perfluoropentanoic acid, perfluorohexanoic acid, perfluoroheptanoic acid, perfluorooctanoic acid, perfluorononanoic acid, perfluorodecanoic acid or perfluorododecanoic acid may be mentioned.

As the polyfluoroalkylcarboxylic acid having an etheric oxygen atom between carbon atoms, for example
$CF_3CF_2OCF_2CF_2OCF_2COOH$,
$CF_3CF_2CF_2OCF(CF_3)COOH$,
$CF_3CF_2CF_2OCF(CF_3)CF_2OCF(CF_3)COOH$,
$CF_3CF_2CF_2[CF(CF_3)CF_2O]_2CF(CF_3)COOH$,
$CF_3CF_2CF_2O[CF(CF_3)CF_2O]_3CF(CF_3)COOH$,
$CF_3CF_2CF_2CF_2CF_2OCF(CF_3)COOH$,
$CF_3OCF(CF_3)CF_2OCF(CF_3)COOH$,
$CF_3OCF_2OCF_2OCF_2OCF_2COOH$,
$CF_3OCF_2CF_2CF_2OCFHCF_2COOH$, or
$CF_3CF_2CF_2OCFHCF_2COOH$ may be mentioned.

As the ω-hydroperfluoroalkylcarboxylic acid, for example, specifically ω-hydroperfluoroheptanoic acid, ω-hydroperfluorooctanoic acid or ω-hydroperfluorononanoic acid may be mentioned.

As the ω-chloroperfluoroalkylcarboxylic acid, for example, specifically ω-chloroperfluoroheptanoic acid, ω-chloroperfluorooctanoic acid or ω-chloroperfluorononanoic acid may be mentioned.

As the perfluoroalkylsulfonic acid, for example, specifically perfluorohexanesulfonic acid, perfluoroheptanesulfonic acid, perfluorooctanesulfonic acid, perfluorononanesulfonic acid or perfluorodecanesulfonic acid may be mentioned.

The fluorinated emulsifier is preferably, in view of excellent stability of the aqueous dispersion containing the fluorinated polymer at the time of production of the aqueous dispersion, an ammonium salt of a $C_{6-12}$ perfluoroalkylcarboxylic acid or an ammonium salt of a $C_{6-12}$ perfluoroalkylcarboxylic acid having an etheric oxygen atom between carbon atoms, more preferably
$CF_3CF_2OCF_2CF_2OCF_2COONH_4$,
$CF_3CF_2CF_2OCF(CF_3)COONH_4$,
$CF_3CF_2CF_2OCF(CF_3)CF_2OCF(CF_3)COONH_4$,
$CF_3CF_2CF_2[CF(CF_3)CF_2O]_2CF(CF_3)COONH_4$,
$CF_3CF_2CF_2O[CF(CF_3)CF_2O]_3CF(CF_3)COONH_4$,
$CF_3CF_2CF_2CF_2CF_2OCF(CF_3)COONH_4$,
$CF_3OCF(CF_3)CF_2OCF(CF_3)COONH_4$, or
$CF_3OCF_2CF_2CF_2OCFHCF_2COONH_4$,
particularly preferably $CF_3CF_2OCF_2CF_2OCF_2COONH_4$.

The concentration of the fluorinated emulsifier in the liquid to be treated is preferably from 10 to 5,000 ppm, more preferably from 10 to 1,000 ppm. When the concentration of the fluorinated emulsifier is at least 10 ppm, the fluorinated emulsifier in the liquid to be treated can be efficiently recovered. When the concentration of the fluorinated emulsifier is at most 5,000 ppm, the life of the strongly basic IER will be long, and the fluorinated emulsifier can be efficiently recovered.

Strongly Basic IER:

The ion exchange capacity of the strongly basic IER is at most 1.0 eq/L, preferably from 0.7 to 1.0 eq/L, more preferably from 0.8 to 1.0 eq/L. When the ion exchange capacity of the strongly basic IER is at most 1.0 eq/L, the fluorinated polymer is less likely to be attached to the strongly basic IER since the amount of ion exchange groups which interact (e.g. react) with the fluorinated polymer tends to be small. When the ion exchange capacity of the strongly basic IER is at least 0.8 eq/L, the fluorinated emulsifier can be more efficiently recovered.

The ion exchange capacity of the strongly basic IER is determined by the method disclosed in Examples.

The water content of the strongly basic IER is at least 60 mass %, preferably from 63 to 80 mass %, more preferably from 63 to 75 mass %. When the water content of the strongly basic IER is at least 60 mass %, hydrophilicity of the strongly basic IER will be high, and the fluorinated polymer is less likely to be attached to the strongly basic IER. Further, the fluorinated emulsifier is likely to be diffused into the inside of particles of the strongly basic IER. When the water content of the strongly basic IER is at most 80 mass %, a decrease in the strength of the particles of the strongly basic IER due to insufficient crosslinking will be suppressed.

The water content of the strongly basic IER is obtained by the method disclosed in Examples.

The ion exchange capacity of the strongly basic IER may be adjusted to be within a desired range by adjusting the number of ion exchange groups.

The water content of the strongly basic IER may be adjusted to be within a desired range e.g. by adjusting the number of ion exchange groups, or by adjusting the crosslink density (the amount of the crosslinking agent (such as divinylbenzene)). However, if the number of ion exchange groups is increased too much, the ion exchange capacity of the strongly basic IER exceeds 1.0 eq/L. Therefore, it is preferred to adjust the water content of the strongly basic IER to be at least 60 mass % by lowering the crosslink density.

The strongly basic IER may be a resin having quaternary ammonium groups on its side chains as ion exchange groups.

The resin main body may, for example, be a styrene/divinylbenzene crosslinked resin, an acrylic/divinylbenzene crosslinked resin or a cellulose resin.

The quaternary ammonium groups may, for example, be trimethylammonium groups ($—N^+(CH_3)_3X^-$) or dimethylethanolammonium groups ($—N^+(CH_3)_2CH_2CH_2OH\ X—$).

Here, $X^-$ is an optional counter anion such as $OH^-$ or $Cl^-$.

The strongly basic IER is particularly preferably a styrene/divinylbenzene crosslinked resin having trimethylammonium groups on its side chains in view of small leakage of ions and excellent chemical stability.

As the strongly basic IER, $OH^-$ type and $Cl^-$ type are commercially available depending upon the type of the counter ion. In recovery of the fluorinated emulsifier in the coagulation waste water by adsorption on the strongly basic IER, the adsorption performance of the IER is determined by the water content and the ion exchange capacity, and accordingly the type of the counter ion is not limited in the present invention.

The strongly basic IER may be a porous type or a gel type, and is preferably a porous type in view of excellent adsorption performance for the fluorinated emulsifier.

The average particle size of the strongly basic IER is preferably from 0.1 to 5 mm, more preferably from 0.2 to 2 mm, particularly preferably from 0.3 to 1.5 mm. When the average particle size of the strongly basic IER is within the above range, the column packed with the strongly basic IER is less likely to be clogged. Here, the average particle size was obtained by a sieving method. An IER sample was placed on a sieve shaker, and the particle size distribution was measured by sieving. The size of the sieve opening corresponding to a residue content of 50% was determined and taken as the average particle size.

Commercially available products of the strongly basic IER may, for example, be DIAION (registered trademark) PA306 manufactured by Mitsubishi Chemical Corporation, LEWATIT (registered trademark) MONOPLUS MP8000H and MP800C1 manufactured by LANXESS, and PUROLITE (registered trademark) A200MBOH, A500POH and A503 manufactured by Purolite K.K. Preferred is MP800OH, MP800CI or A500POH, which is excellent in the adsorption performance for the fluorinated emulsifier and is less susceptible to influence of the SS components, and particularly preferred is MP800OH or MP800CI.

The ratio (the strongly basic IER/the liquid to be treated) of the strongly basic IER to the liquid to be treated is preferably from 1/100 to 1/5,000 (mass ratio), more preferably from 1/100 to 1/2,000 (mass ratio). When the mass of the liquid to be treated is at least 100 times the mass of the strongly basic IER, the fluorinated emulsifier can be recovered in a short time. When the mass of the liquid to be treated is at most 5,000 times the mass of the strongly basic IER, the life of the strongly basic IER tends to be long, and the fluorinated emulsifier can be efficiently recovered.

(Step (b))

As a method of eluting the fluorinated emulsifier adsorbed on the strongly basic IER from the strongly basic IER, a known method for regenerating a strongly basic IER may be mentioned.

As a method of eluting the fluorinated emulsifier adsorbed on the strongly basic IER from the strongly basic IER and further recovering the eluted fluorinated emulsifier, for example, the following method may be mentioned.

(α) A method of bringing the strongly basic IER into contact with a mixture of an aqueous inorganic acid solution, a fluorinated medium and a non-fluorinated medium, separating and recovering the liquid phase from the strongly basic IER, and recovering an acid of the fluorinated emulsifier from the liquid phase.

(β) A method of bringing the strongly basic IER into contact with an aqueous inorganic acid solution, then bringing the strongly basic IER into contact with a mixture of a fluorinated medium and a non-fluorinated medium, separating and recovering the liquid phase from the strongly basic IER, and recovering an acid of the fluorinated emulsifier from the liquid phase.

The aqueous inorganic acid solution may, for example, be hydrochloric acid, sulfuric acid, nitric acid or phosphoric acid, and is preferably hydrochloric acid in view of handling efficiency.

The fluorinated medium may, for example, be hydrochlorofluorocarbon, hydrofluorocarbon, hydrofluoroether or hydrofluoroalcohol, preferably hydrochlorofluorocarbon, hydrofluorocarbon or hydrofluoroether.

The non-fluorinated medium may, for example, be an alcohol, a ketone, a nitrile, an ether, an ester, an amide, a pyrrolidone or a sulfoxide, and is preferably acetone or acetonitrile.

Method (α):

The ratio (the strongly basic IER/the mixture) of the strongly basic IER to the mixture is preferably from 1/99 to 99/1 (mass ratio), more preferably from 10/90 to 90/10 (mass ratio), particularly preferably from 15/85 to 50/50 (mass ratio).

The ratio (the aqueous inorganic acid solution/the fluorinated medium) of the aqueous inorganic acid solution to the fluorinated medium is preferably from 1/99 to 95/5 (mass ratio), more preferably from 5/95 to 80/20 (mass ratio), particularly preferably from 10/90 to 70/30 (mass ratio).

The ratio (the fluorinated medium/the non-fluorinated medium) of the fluorinated medium to the non-fluorinated medium is preferably from 5/95 to 95/5 (mass ratio), more preferably from 10/90 to 95/5 (mass ratio), particularly preferably from 15/85 to 95/5 (mass ratio).

The time of contact between the strongly basic IER and the mixture is preferably from 5 to 500 minutes, more preferably from 10 to 300 minutes.

Method (β):

The ratio (the strongly basic IER/the aqueous inorganic acid solution) of the strongly basic IER to the aqueous inorganic acid solution is preferably from 99/1 to 1/99 (mass ratio), more preferably from 90/10 to 10/90 (mass ratio), particularly preferably from 60/40 to 30/70 (mass ratio).

The time of contact between the strongly basic IER and the aqueous inorganic acid solution is preferably from 5 to 500 minutes, more preferably from 10 to 300 minutes.

The ratio (the fluorinated medium/the non-fluorinated medium) of the fluorinated medium to the non-fluorinated medium is preferably from 5/95 to 95/5 (mass ratio), more preferably from 10/90 to 90/10 (mass ratio), particularly preferably from 20/80 to 90/10 (mass ratio).

The ratio (the strongly basic IER/the mixture) of the strongly basic IER to the mixture is preferably from 1/99 to 80/20 (mass ratio), more preferably from 10/90 to 70/30 (mass ratio), particularly preferably from 15/85 to 60/40 (mass ratio).

The time of contact between the strongly basic IER and the mixture is preferably from 5 to 500 minutes, more preferably from 10 to 300 minutes.

(Function and Effects)

In the above-described method for recovering a fluorinated emulsifier of the present invention, as the strongly basic IER on which the fluorinated emulsifier is to be adsorbed, a strongly basic IER having an ion exchange capacity of at most 1.0 eq/L and a water content of at least 60 mass % is used. Accordingly, SS components consisting of a fluorinated polymer contained in a liquid to be treated are less likely to be attached to the strongly basic IER, and the fluorinated emulsifier (in the case of an anionic fluorinated emulsifier, anion of an acid) is easily diffused into the interior of particles of the strongly basic IER. That is, the ion exchange rate between the counter ions and the fluorinated emulsifier is higher than the rate of attaching of the SS components to the strongly basic IER surface, whereby the surface of the strongly basic IER is less likely to be covered with the SS components, and a column packed with the strongly basic IER is less likely to be clogged, and the adsorption performance of the strongly basic IER is less likely to decrease. As a result, from a liquid to be treated containing a fluorinated polymer and a fluorinated emulsifier, the fluorinated emulsifier can be efficiently recovered.

Further, in the above-described method for recovering a fluorinated emulsifier of the present invention, the surface of the strongly basic IER is less likely to be covered with SS components consisting of a fluorinated polymer contained in a liquid to be treated even without pretreatment of the liquid to be treated. Accordingly, it is not necessary to pretreat the liquid to be treated, and from the liquid to be treated containing a fluorinated polymer and a fluorinated emulsifier, the fluorinated emulsifier can be easily recovered.

The method for recovering a fluorinated emulsifier of the present invention is applicable not only to recovery of a fluorinated emulsifier but also to recovery of a low molecular fluorinated carboxylic acid (such as trifluoroacetic acid or pentafluoropropanoic acid) or its salt and a low molecular fluorinated sulfonic acid (such as trifluoromethanesulfonic acid) or its salt.

EXAMPLES

Now, the present invention will be described in further detail with reference to Examples. However, it should be understood that the present invention is by no means restricted to such specific Examples. ppm and % are represented based on mass, unless otherwise specified.

Ex. 1 to 3 are Examples of the present invention, and Ex. 4 and 5 are Comparative Examples.

(Concentration of Fluorinated Emulsifier)

The concentration of $CF_3CF_2OCF_2CF_2OCF_2COONH_4$ (hereinafter referred to as SAA1) as a fluorinated emulsifier was measured by a colorimetric method using methylene blue.

To about 500 mL of water, 12 g of concentrated sulfuric acid at a concentration of about 18 mol/L was gradually added and cooled, and 0.03 g of methylene blue and 50 g of anhydrous sodium sulfate were dissolved, and water was added to prepare 1 L (liter) of a methylene blue solution. 4 mL of the methylene blue solution and 5 mL of chloroform were put in a test tube, and 0.1 g of a 1,000 to 3,000-fold diluted liquid having 0.1 g of a sample containing SAA1 diluted with 100 to 300 mL of water, was added, vigorously shaken, and left at rest. The lower chloroform phase was collected and subjected to filtration through a filter with a pore size of 0.2 μm, and the absorbance at 630 nm was measured by a spectrophotometer. The chloroform phase turns bluish depending upon the content of SAA1. The concentration of SAA1 in the sample was determined using a calibration curve prepared by measuring the absorbance in the same method using 0.1 g of a SAA1 aqueous solution having a known concentration.

(Concentration SS Components)

10 g of a sample containing SS components was put in a halogen moisture analyzer (manufactured by Mettler-Toredo International Inc., HR-73) and dried at 200° C. until the mass became constant, and the residue on evaporation was taken as SS components. SAA1 sublimates or evaporates at 200° C., and is not included in the SS components.

(Method for Preparing Standardized Sample)

About 20 mL of a sample (strongly basic IER) was packed in a resin column and washed by passing 1,500 mL of a 2N—NaOH aqueous solution and then 1 L of demineralized water. Then, 500 mL of a 5% NaCl aqueous solution was passed to convert the strongly basic IER to a Cl-form, and then demineralized water was passed to wash the strongly basic IER until the cleaning liquid became neutral as tested with phenolphthalein.

(Ion Exchange Capacity of Strongly Basic IER)

10 mL of the standardized sample was measured by a measuring cylinder, put in the resin column and regenerated with 750 mL of a 2N—NaOH aqueous solution. Then, it was washed with 1 L of demineralized water, and 250 mL of a 5% NaCl aqueous solution was passed, the eluate was put in a measuring flask, 50 mL thereof was measured and titrated with a 0.1 N—HCl aqueous solution using a methyl red/methylene blue mixed indicator, and the ion exchange capacity (meq/m L) was calculated from the following formula and calculated as eq/L.

Ion exchange capacity (meq/mL)=((amount (mL) of 0.1 N—HCl consumed for titration)×(HCl titer)×0.1×250/50)/10

(Water Content of Strongly Basic IER)

10 mL of the standardized sample was accurately measured by a measuring cylinder, and the resin was wrapped with cloth and subjected to centrifugal separation to remove attached water, and the mass of the resin was quickly measured. Then, the resin was dried in a constant temperature dryer at 105° C. for 4 hours and left in a desiccator for 30 minutes to cool, and the mass of the resin after drying was weighed to calculate the water content.

Water content (%)=(the mass (g) of the resin before drying—the mass (g) of the resin after drying)/the mass (g) of the resin before drying×100

(Rate of Adsorption for Fluorinated Emulsifier)

The rate of adsorption of the IER was calculated from the following formula.

Rate of adsorption (%)=[(the SAA1 concentration in the coagulation waste water before the step (a))−(the SAA1 concentration in the coagulation waste water after the step (a))]/(the SAA1 concentration in the coagulation waste water before the step (a))×100

(Performance)

The performance was calculated from the following formula.

Performance (mL/g)=(the amount (mL) of the coagulation waste water treated until immediately before the rate of adsorption of the strongly basic IER decreases to be below 99%)/(the amount (g) of the strongly basic IER used)

(Coagulation Water Water)

TFE was subjected to emulsion polymerization in an aqueous dispersion medium in the presence of SAA1 to obtain an aqueous dispersion of PTFE. PTFE in the aqueous dispersion was coagulated and separated to obtain a coagulation waste water. In the coagulation waste water, the concentration of SS components mainly consisting of non-coagulated PTFE fine particles was 1,900 ppm, the concentration of SAA1 was 420 ppm, and the pH of the coagulation waste water was 4.60.

Ex. 1

Step (a):

Into a 500 mL glass beaker equipped with a propeller blade, 210 mL of a coagulation waste water was put, and 5 g of a strongly basic IER (manufactured by LANXESS, MP800C1) was added. The coagulation waste water was stirred at a number of revolutions of 250 rpm for 1 hour, so that SAA1 in the coagulation waste water was adsorbed on the strongly basic IER. One hour later, the coagulation waste water was subjected to filtration through a 200 mesh sheet made of SUS to separate MP800CI and SS components coagulated by this operation, from the filtrate. The concentration of SAA1 in the filtrate was measured.

Into a 500 mL glass beaker equipped with a propeller blade, 210 mL of a new coagulation waste water was put, and MP800Cl and the SS components collected by filtration by the above operation were added. The coagulation waste water was stirred at a number of revolutions of 250 rpm for 1 hour. Such an operation was repeated until the rate of adsorption for SAA1 decreased to be below 99%, and the amount of the treated coagulation waste water was confirmed. As a result, the amount of the coagulation waste water treated until immediately before the rate of adsorption for SAA1 decreased to be below 99%, was 2,940 mL in total (14 batches). The surface of MP800Cl after treatment was observed by a microscope (manufactured by KEYENCE CORPORATION, VHX-200, the same applies hereinafter), whereupon attachment of the SS components was not observed. The SS components were coagulated to each other to form agglomerates.

Ex. 2

The same operation as in Ex. 1 was carried out except that MP8000H manufactured by LANXESS was used as the strongly basic IER. As a result, the amount of the coagulation waste water treated until immediate before the rate of adsorption for SAA1 decreased to be below 99% was 3,150 mL in total (15 batches). The surface of MP8000H after treatment was observed with the microscope, whereupon attachment of the SS components was not observed.

Ex. 3

The same operation as in Ex. 1 was carried out except that A500POH manufactured by Purolite K.K. was used as the strongly basic IER. As a result, the amount of the coagulation waste water treated until immediate before the rate of adsorption for SAA1 decreased to be below 99% was 1,050 mL in total (5 batches). The surface of A500POH after treatment was observed with the microscope, whereupon attachment of the SS components was not observed.

Ex. 4

The same operation as in Ex. 1 was carried out except that A200MBOH manufactured by Purolite K.K. was used as the strongly basic IER. As a result, the amount of the coagulation waste water treated until immediate before the rate of adsorption for SAA1 decreased to be below 99% was 420 mL in total (2 batches). The surface of A200MBOH after treatment was observed with the microscope, whereupon the SS components were attached to cover the surface of A200MBOH.

Ex. 5

The same operation as in Ex. 1 was carried out except that MP6000H manufactured by LANXESS K.K. was used as the strongly basic IER. As a result, the amount of the coagulation waste water treated until immediate before the rate of adsorption for SAA1 decreased to be below 99% was 210 mL in total (1 batch). The surface of MP6000H after treatment was observed with the microscope, whereupon the SS components were attached to cover the surface of MP6000H.

The above results are shown in Table 1.

TABLE 1

| | Emulsifier | Ion exchange resin | Resin structure | Water content [%] | Ion exchange capacity [eq/L] | Amount of IER used [g] | Number of batches [times] | Amount of waste water treated [mL] | Performance [mL/g] (waste water g/IER g) |
|---|---|---|---|---|---|---|---|---|---|
| Ex. 1 | SAA1 | MP800Cl | Porous | 72.5 | 0.8 | 5 | 14 | 2940 | 588 |
| Ex. 2 | SAA1 | MP800OH | Porous | 72.5 | 0.8 | 5 | 15 | 3150 | 630 |
| Ex. 3 | SAA1 | A500POH | Porous | 66.5 | 0.8 | 5 | 5 | 1050 | 210 |
| Ex. 4 | SAA1 | A200MBOH | Gel | 45.5 | 1.1 | 5 | 2 | 420 | 84 |
| Ex. 5 | SAA1 | MP600OH | Porous | 57.5 | 1.1 | 5 | 1 | 210 | 42 |

INDUSTRIAL APPLICABILITY

The method for recovering a fluorinated emulsifier of the present invention is useful for treatment of a waste water containing a fluorinated emulsifier. The fluorinated emulsifier recovered by the present invention may be recycled e.g. for emulsion polymerization of a fluorinated monomer as it is or after neutralized.

This application is a continuation of PCT Application No. PCT/JP2014/076728 filed on Oct. 6, 2014, which is based upon and claims the benefit of priority from Japanese Patent Application No. 2013-212673 filed on Oct. 10, 2013. The contents of those applications are incorporated herein by reference in their entireties.

What is claimed is:

1. A method comprising:
bringing a liquid comprising a fluorinated polymer and a fluorinated emulsifier and a strongly basic anion exchange resin having an ion exchange capacity of at most 1.0 eq/L and a water content of at least 60 mass % into contact with each other, so that the fluorinated emulsifier is adsorbed on the strongly basic anion exchange resin, to recover the fluorinated emulsifier from the liquid.

2. The method according to claim 1, further comprising:
eluting the fluorinated emulsifier from the strongly basic anion exchange resin after the fluorinated emulsifier is adsorbed on the strongly basic anion exchange resin.

3. The method for according to claim 1, wherein the liquid is a waste water, obtained by coagulating the fluorinated polymer in the aqueous dispersion comprising the fluorinated polymer and the fluorinated emulsifier to form coagulum and removing the coagulum.

4. The method according to claim 1, wherein the concentration of the fluorinated emulsifier in the liquid is from 10 to 5,000 ppm.

5. The method according to claim 1, wherein the ratio of the strongly basic anion exchange resin to the liquid (the strongly basic anion exchange resin/the liquid) is from 1/100 to 1/5,000 by mass.

6. The method according to claim 1, wherein the fluorinated emulsifier is a fluorinated carboxylic acid, a fluorinated sulfonic acid, a salt of a fluorinated carboxylic acid, or a salt of a fluorinated sulfonic acid.

7. The method according to claim 6, wherein the fluorinated carboxylic acid is a perfluoroalkylcarboxylic acid or a compound in which an etheric oxygen atom is inserted between carbon atoms in a perfluoroalkylcarboxylic acid.

8. The method according to claim 1, wherein the counter ion of the strongly basic anion exchange resin is $OH^-$ or $Cl^-$.

9. The method according to claim 1, wherein the strongly basic anion exchange resin has quaternary ammonium groups on its side chains as ion exchange groups.

10. The method according to claim 1, wherein the average particle size of the strongly basic anion exchange resin is from 0.1 to 5 mm.

11. The method according to claim 1, wherein the concentration of the fluorinated emulsifier in the liquid is from 10 to 1,000 ppm.

12. The method according to claim 1, wherein the ratio of the strongly basic anion exchange resin to the liquid (the strongly basic anion exchange resin/the liquid) is from 1/100 to 1/2,000 by mass.

13. The method according to claim 1, wherein the average particle size of the strongly basic anion exchange resin is from 0.3 to 5 mm.

14. The method according to claim 1, wherein the ion exchange capacity of the strongly basic anion exchange resin is from 0.7 to 1.0 eq/L.

15. The method according to claim 1, wherein the ion exchange capacity of the strongly basic anion exchange resin is from 0.8 to 1.0 eq/L.

16. The method according to claim 1, wherein the water content of the strongly basic anion exchange resin is from 63 to 80 mass %.

17. The method according to claim 1, wherein the water content of the strongly basic anion exchange resin is from 63 to 75 mass %.

18. The method according to claim 1, wherein the strongly basic anion exchange resin is a styrene/divinylbenzene crosslinked resin having trimethylammonium groups on a side chain thereof.

19. The method according to claim 1, wherein the liquid further comprises a suspended solid component.

20. The method according to claim 19, wherein a treatment of reducing an amount of the suspended solid component in the liquid is not conducted before bringing the liquid and the strongly basic anion exchange resin into contact with each other.

* * * * *